United States Patent
Yamaguchi et al.

(10) Patent No.: US 9,034,164 B2
(45) Date of Patent: May 19, 2015

(54) PARTICLE CHARACTERIZATION CELL AND PARTICLE CHARACTERIZATION INSTRUMENT

(75) Inventors: Tetsuji Yamaguchi, Kyoto (JP); Makoto Nagura, Kyoto (JP)

(73) Assignee: HORIBA, LTD. (JP)

(*) Notice: Subject to any disclaimer, the term of this patent is extended or adjusted under 35 U.S.C. 154(b) by 843 days.

(21) Appl. No.: 13/220,813

(22) Filed: Aug. 30, 2011

(65) Prior Publication Data

US 2012/0048737 A1     Mar. 1, 2012

(30) Foreign Application Priority Data

Aug. 31, 2010   (JP) .................................. 2010-193665

(51) Int. Cl.
    *G01N 1/10*     (2006.01)
    *G01N 21/51*     (2006.01)
(52) U.S. Cl.
    CPC .......... *G01N 21/51* (2013.01); *G01N 2021/513* (2013.01)
(58) Field of Classification Search
    USPC ................................................. 204/645, 600
    See application file for complete search history.

(56) References Cited

U.S. PATENT DOCUMENTS 6,264,814 B1 *   7/2001   Lange ........................... 204/450

FOREIGN PATENT DOCUMENTS

| CN | 2148961 Y | 12/1993 |
|---|---|---|
| CN | 101169363 A | 4/2008 |
| CN | 102159934 A | 8/2011 |
| JP | 61-277047 A | 12/1986 |
| JP | 4-66572 A | 6/1992 |
| JP | 2002-504232 A | 2/2002 |
| JP | 2010-101705 A | 5/2010 |
| JP | 2011-75537 A | 4/2011 |
| WO | 9219960 A | 11/1992 |
| WO | 02/08748 A2 | 1/2002 |

OTHER PUBLICATIONS

Office Action dated Jun. 9, 2014 issued in Chinese patent application No. 201110251703.8, with English translation.
Extended European Search Report for Application No. 11007043.0-2204, dated Dec. 9, 2011.

* cited by examiner

*Primary Examiner* — Arun S Phasge
(74) *Attorney, Agent, or Firm* — Cantor Colburn LLP (57) ABSTRACT

The present invention is configured to be provided with: a bottom-equipped tubular cell main body that forms an internal space S1 that extends in a longer direction, and has one end part that is opened; a pair of applying electrodes that are arranged so as to face to each other in the internal space; and a fixing spacer that intervenes between the pair of applying electrodes to thereby define a distance between the applying electrodes, and fixes the pair of applying electrodes, wherein in a state where the fixing spacer is inserted into the cell main body, in a lower part of the internal space of the cell main body, a zeta potential measuring space in which the pair of applying electrodes are exposed is formed.

5 Claims, 8 Drawing Sheets

PARTICLE CHARACTERIZATION CELL AND PARTICLE CHARACTERIZATION INSTRUMENT

TECHNICAL FIELD

The present invention relates to a particle characterization cell or particle characterization instrument that is intended to measure physical property values of particles such as a zeta potential.

BACKGROUND ART

Polymers or colloidal particles corresponding to aggregates of polymers are, in an aqueous solution, charged by adsorption of dissociation groups or ions. A potential formed by the charging is referred to as a zeta potential ($\zeta$) and the zeta potential is calculated by applying an electric field to particles and measuring a migration velocity (electrophoretic velocity) of the particles.

Also, to use an electrophoretic velocity measuring instrument to measure the zeta potential, as disclosed in Patent literature 1 or 2, by inserting electrodes into a measuring cell that contains a liquid sample in which the particles are dispersed; irradiating the particles with laser light while applying DC voltage between the electrodes to apply an electric field to the particles in the liquid sample; receiving scattered light that is scattered at a predetermined angle; and measuring a difference in frequency (interference phenomenon) between the scattered light and the reference light obtained by branching part of the laser light, the migration velocity of the particles in the liquid sample is calculate. Then, by performing a predetermined calculation process on the obtained migration velocity, the zeta potential is calculated.

As a conventional zeta potential measuring cell, as disclosed in Patent literature 1 or as illustrated in FIG. 9 of Patent literature 1, there is one that has: a bottom-equipped tubular cell main body that contains the liquid sample; and an electrode sensor that is inserted into the cell main body. The electrode sensor has a pair of applying electrodes, and a sensor main body in which the applying electrodes are buried, and is configured such that by fitting the sensor main body into the cell main body, the pair of applying electrodes comes into contact with the liquid sample contained in the cell main body.

In the zeta potential measuring cell, current is applied to the pair of applying electrodes, so that on the applying electrodes, a redox reaction occurs, and thereby ions in the liquid sample are precipitated and attached to the applying electrodes. Also, in the case where the liquid sample is one that contains protein or the like, the protein is attached to the electrodes. For this reason, before the measurement or on another occasion, cleaning to remove attached substances from the applying electrodes should be performed.

However, the electrode sensor having the above configuration is integrally configured by burying the pair of applying electrodes into the sensor main body, and therefore in order to remove the substances attached to the applying electrodes, a whole of the electrode sensor should be detached from the cell main body and then cleaned. If so, there occurs a problem that the sensor main body becomes impeditive, and this makes it difficult to clean the electrodes. Also, in the case of replacing only the electrodes by new ones, the electrode sensor itself should be replaced, which gives rise to a problem in cost.

Further, in the case of replacing the electrodes by applying electrodes that undergo surface treatment or are made of a different material corresponding to the type of the liquid sample, the electrode sensor itself should also be replaced, which also gives rise to a problem of increased manufacturing cost.

CITATION LIST

Patent Literature

[Patent literature 1] WA 2010-101705

SUMMARY OF INVENTION

Technical Problem

Therefore, the present invention is made to solve the above problems at once, and has a main desired object to not only enable a single body of applying electrode to be replaced to make it easy to clean the applying electrodes, but also enable old applying electrodes to be replaced by new applying electrodes, or enable applying electrodes to be replaced in accordance with the type of a liquid sample, and also simplify corresponding assembling work.

Solution to Problem

That is, a particle characterization cell according to the present invention is one that is used for a particle characterization instrument that measures physical properties of particles dispersed in a liquid sample, and configured to be provided with: a bottom-equipped tubular cell main body that forms an internal space that extends in a longer direction, and has a longer direction one end part that is opened; a pair of applying electrodes that are inserted into the cell main body from the longer direction one end part and arranged so as to face to each other in the internal space; and a fixing spacer that is inserted into the cell main body from the longer direction one end part, intervenes between the pair of applying electrodes to thereby define a distance between the applying electrodes, and presses the pair of applying electrodes against an inner surface of the cell main body to thereby fix the pair of applying electrodes, wherein in a state where the fixing spacer is inserted into the cell main body, in a lower part of a containing space of the cell main body, a particle characterization space in which the pair of applying electrodes are exposed is formed.

If so, the applying electrodes and the fixing spacer can be individually detached from the cell main body, and therefore cleaning work for the applying electrodes can be simplified. Also, in the case where it is necessary to replace the applying electrodes, such as the case where dirt of the applying electrodes cannot be removed, the applying electrodes can be replaced as a single body, and therefore the applying electrodes can be replaced at low cost. In this case, only by inserting the pair of applying electrodes and fixing spacer into the cell main body, the particle characterization space is formed in the cell main body, and therefore assembling of the particle characterization cell is easy. Further, the applying electrodes that undergo different surface treatment or are made of a different material corresponding to the type of the liquid sample can be manufactured as a single body; the replacement thereof is also easy; and the particle characterization cell specialized for the type of any of various liquid samples can be easily manufactured.

In order for the particle characterization space to be formed only by inserting the fixing spacer into the cell main body without considering an insertion position of the fixing spacer with respect to the cell main body, desirably, the fixing spacer has an insertion part that is to be inserted into the cell main body, and an engaging part that, in a state where the insertion part is inserted into the cell main body, engages with the longer direction one end part; and the insertion part is configured to be shorter than a longer direction length of the internal space.

In order to enable, after the applying electrodes have been fixed to the cell main body by the fixing spacer, the liquid sample to be introduced into the particle characterization space, and also enable both of batch type measurement and flow type measurement to be accommodated, desirably, the fixing spacer has a sample introduction path that externally introduces the liquid sample into the particle characterization space.

Advantageous Effects of Invention

According to the present invention configured as described, not only a single body of applying electrodes can be replaced to make it easy to clean the applying electrodes, but also old applying electrodes can be replaced by new applying electrodes, or applying electrodes can be replaced in accordance with the type of a liquid sample, and also corresponding assembling work can be simplified.

DESCRIPTION OF EMBODIMENTS

One embodiment of a zeta potential measuring instrument according to the present invention will hereinafter be described referring to the drawings.

Figure 1:
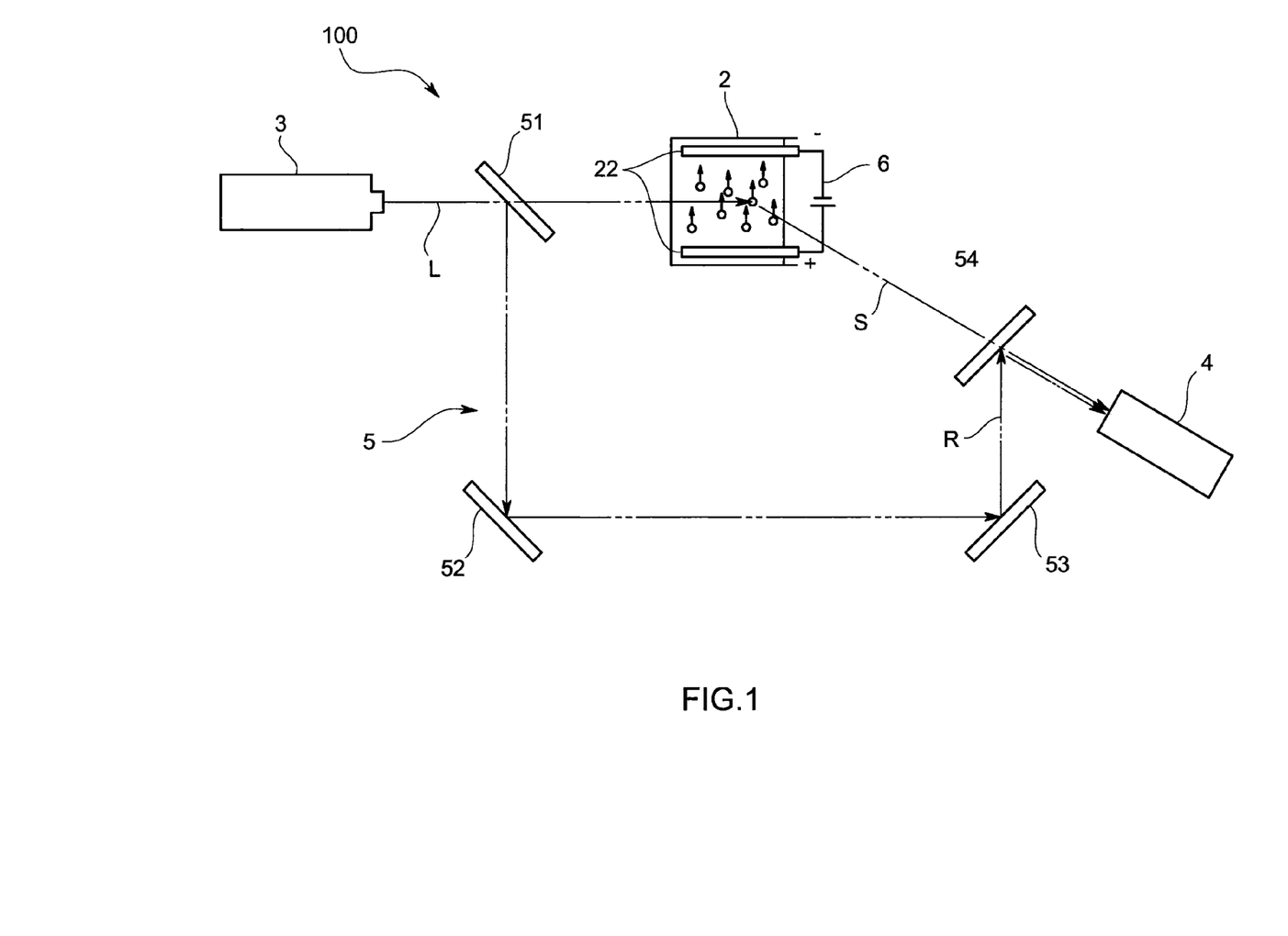
FIG. 1 is a schematic diagram illustrating a configuration of a zeta potential measuring instrument according to one embodiment of the present invention.
Figure 2:
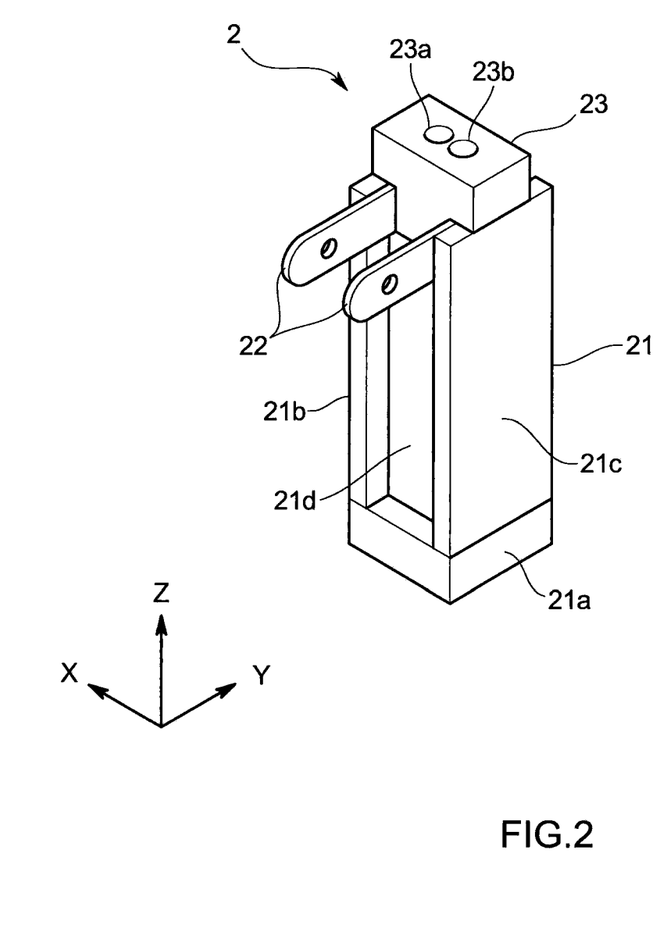
FIG. 2 is a perspective view of a zeta potential measuring cell according to the same embodiment.

A zeta potential measuring instrument 100 according to the present embodiment is, as illustrated in FIG. 1, provided with: a zeta potential measuring cell (hereinafter simply referred to as a measuring cell) 2 that contains a liquid sample adapted to disperse a particle group into a dispersion medium such as water and also has applying electrodes 22 that apply voltage to the liquid sample; a laser light source 3 that irradiates the liquid sample contained in the measuring cell 2 with laser light L; a light detecting part 4 that receives scattered light S emitted from the particle group in the liquid sample irradiated with the laser light L, and includes a photomultiplier and the like that output a pulse signal depending on the number of photons of the scattered light S or an electrical signal depending on fluctuation in light intensity; and a reference optical system 5 that has a half mirror 51 that branches part of the laser light L emitted from the laser light source 3, mirrors 52 and 53, and a half mirror 54 that mixes reference light R from the mirror 53 and the scattered light S with each other. In this case, the reference light R may be modulated.

Note that the zeta potential measuring instrument 100 of the present embodiment is configured such that the laser light source 3, the light detecting part 4, and the reference optical system 5 are contained in an instrument main body (not illustrated), and the measuring cell 2 can be attached/detached to/from the instrument main body.

Also, in the case of measuring a zeta voltage with the zeta potential measuring instrument 100, by using an electrophoresis method; applying DC or AC voltage between the applying electrodes 22 provided in the measuring cell 2; irradiating particles in the liquid sample with the laser light L while applying an electric field; receiving the scattered light S scattered at a predetermined angle; and measuring a difference in frequency (interference phenomenon) between the scattered light S and the reference light R, a migration velocity of the particles in the liquid sample is calculated. Further, by performing a predetermined calculation process on the obtained migration velocity, the zeta potential is calculated.

Meanwhile, the measuring cell 2 of the present embodiment is, as illustrated in FIGS. 2 to 7, provided with: a bottom-equipped tubular cell main body 21 that forms an internal space S1 that extends in a longer direction, and has a longer direction one end part 21x that is opened; the pair of applying electrodes 22 that are inserted into the cell main body 21 from the longer direction one end part 21x, and arranged so as to face to each other in the internal space S1; and a fixing spacer 23 that is inserted into the cell main body 21 from the longer direction one end part 21x, intervenes between the pair of applying electrodes 22 to thereby define a distance between the applying electrodes 22, and presses the pair of applying electrodes 22 against an inner surface of the cell main body 21 to thereby fix them.

In the following, the respective components 21 to 23 are described referring to FIGS. 2 to 7.

The cell main body 21 is formed of a transparent material such as quartz glass having corrosion resistance to the liquid sample such as organic solvent. Also, the cell main body 21 is, as illustrated in FIGS. 2 to 5, configured to have a bottom wall part 21a, plate-like left and right side wall parts 21b and 21c that face to each other in an X axis direction, and plate-like front and back side wall parts 21d and 21e that face to each other in a Y axis direction, and the bottom-equipped tubular one of which the longer direction one end part (Z axis direction upper part) 21x is opened. The cell main body 21 configured as described forms the internal space S1 (see FIG. 3) that is configured to have the bottom wall part 21, left and right side wall parts 21b and 21c, and front and back side wall parts 21d and 21e, and uniform cross-sectional rectangular shaped. Note that in the case of forming the respective wall parts 21a to 21e from quartz glass, they are fabricated by glass welding so as to be resistant to strength at the time of cleaning.

Figure 4:
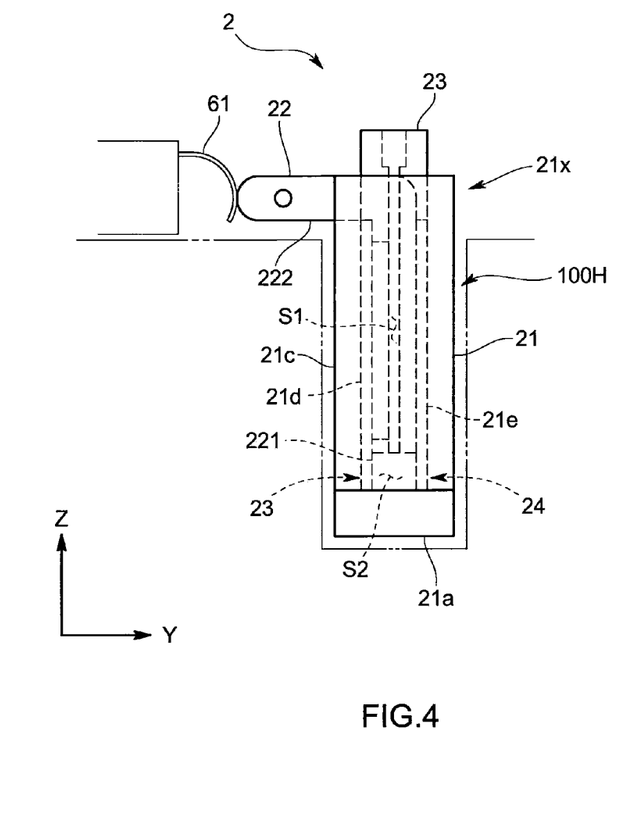
FIG. 4 is a side view of the zeta potential measuring cell according to the same embodiment.

Also, the cell main body 21 is, as illustrated in FIG. 4 and other drawings, formed with: in a state where the measuring cell 2 is attached to a cell placement part 100H of the instrument main body, a light introduction window 23 that introduces the laser light L from the laser light source 3 into an after-mentioned zeta potential measuring space S2; and a light lead-out window for leading the scattered light S having passed through the zeta potential measuring space S2 to the light detecting part 4. The light introduction window 23 and light lead-out window 24 are respectively formed in the front and back side wall parts 21d and 21e that face to each other in the Y axis direction. Specifically, the light introduction window 23 and the light lead-out window 24 are formed in the front and back side wall parts 21d and 21e that form side surfaces of the after-mentioned zeta potential measuring space S2.

Figure 3:
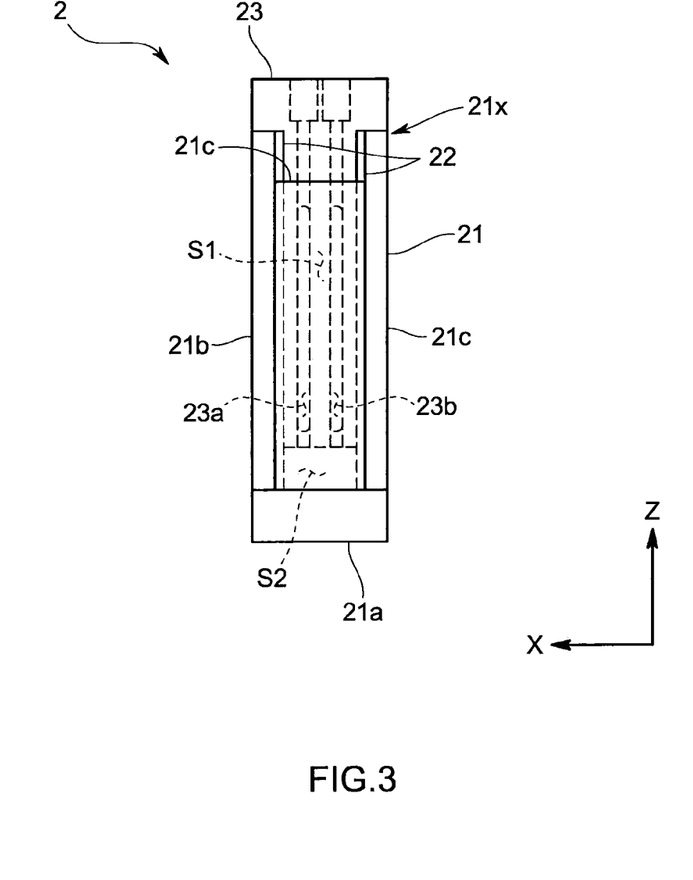
FIG. 3 is a front view of the zeta potential measuring cell according to the same embodiment.
Figure 5:
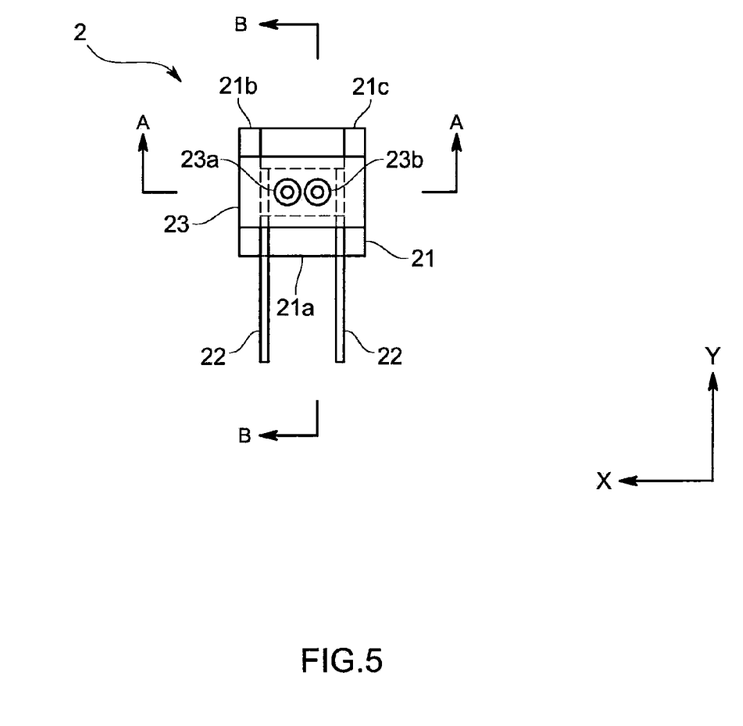
FIG. 5 is a plan view of the zeta potential measuring cell according to the same embodiment.
Figure 6:
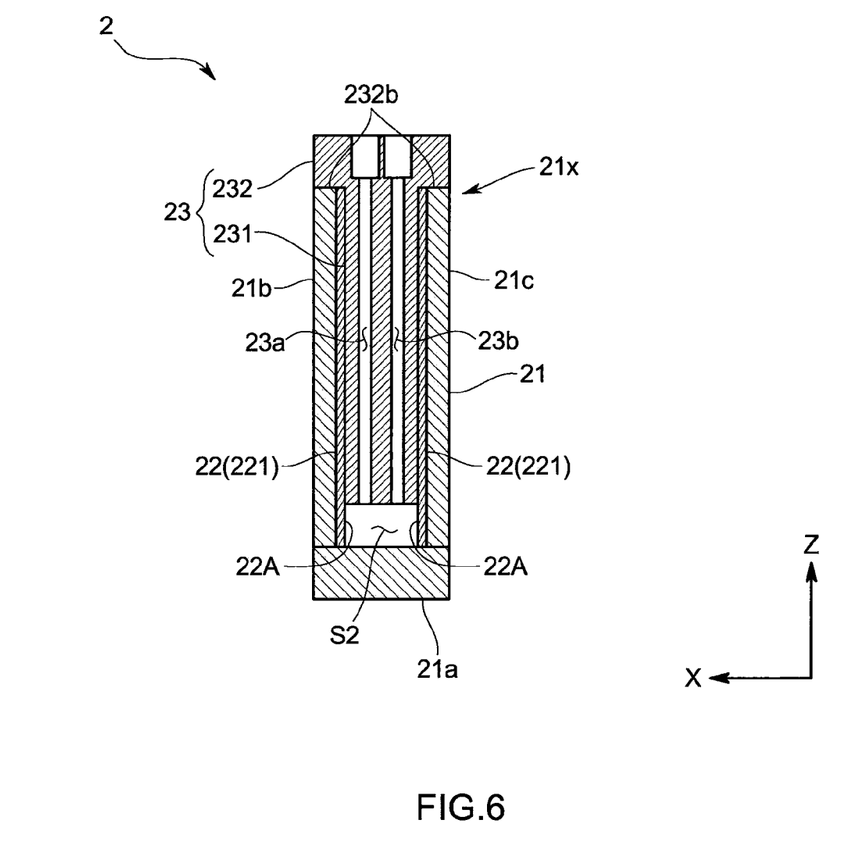
FIG. 6 is an A-A line cross sectional view of the zeta potential measuring cell according to the same embodiment.

The pair of applying electrodes 22 are, as illustrated in FIGS. 3, 5, and 6, inserted into the cell main body 21 from the longer direction one end part 21x, and arranged in the internal space S1 so as to face to each other in the X axis direction. Also, each of the pair of applying electrodes 22 has a long-sized plate-like shape made of, for example, platinum, and the pair of applying electrodes 22 have mutually the same shape, and are, in the present embodiment, as illustrated in FIG. 4, substantially L-shaped in a side view. Also, vertical parts 221 of the applying electrodes 22 are inserted into the cell main body 21. Further, horizontal parts (bent parts) 22 of the applying electrodes 22 are, in the state where the measuring cell 2 is attached to the cell placement part 100H of the instrument main body, in contact with applying terminals 61 of a voltage applying circuit provided on the instrument main body side.

Note that, as the applying electrodes 22, ones that are made of any of various materials and/or undergo any of various processes can be used depending on any of various liquid samples. For example, in the case of using the applying electrodes 22 in organic solvent, it is desirable to use gold. To make the particles migrate in the organic solvent, a high voltage should be applied; however, in the case of using gold for the applying electrodes 22, a resistance value is small and highly electrically conductive, which prevents heat from being generated, and therefore it is possible to make it difficult to damage the liquid sample. Also, in the case of using the applying electrodes 22 under water, it is desirable to use carbon or diamond. Under water containing salt, polarization resistances are likely to occur on electrode surfaces, and therefore electrophoresis corresponding to the applying electrodes 22 is unlikely to occur. In this case, such a material having large electrode surface areas can reduce the polarization resistances, and therefore the particles can be made to migrate according to an applied voltage. In particular, by using carbon for the applying electrodes 22, even at the time of measuring the liquid sample having a high salt concentration, the applying electrodes 22 can be increased in lifetime, and the polarization resistances can be further reduced. Further, by making the electrode surfaces rough with use of acid etching or alkali etching, the applying electrodes 22 can also be made to have the same effect. The etching is performed by applying current to the applying electrodes 22 in acid or alkali.

Figure 7:
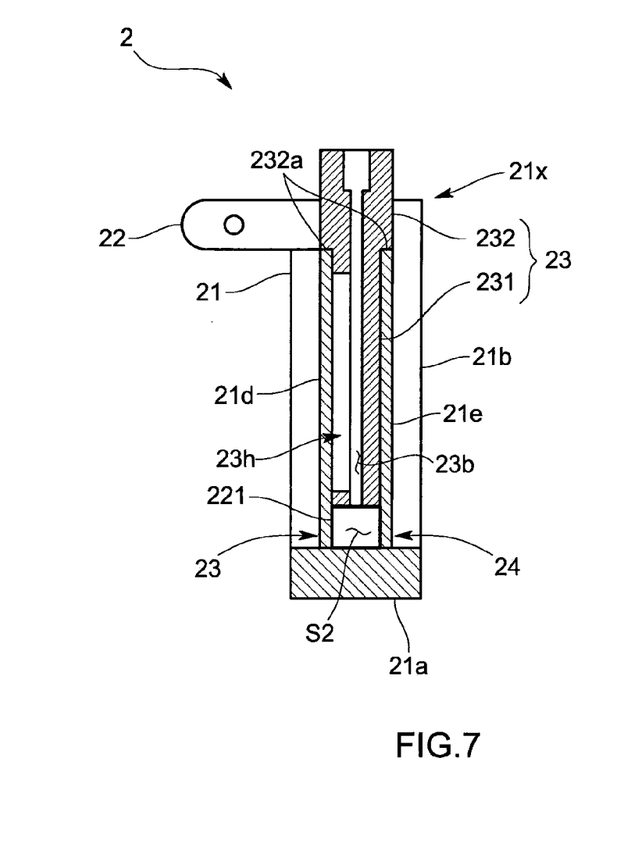
FIG. 7 is a B-B line cross sectional view of the zeta potential measuring cell according to the same embodiment.

Each of the vertical parts 221 of the applying electrodes 22 has substantially the same length as a longer direction length of the internal space S1 formed in the cell main body 21. That is, each of the vertical parts 221 of the applying electrodes 22 is configured to, in a state where the vertical part 221 is inserted into the cell main body 21, extend to a lower surface (bottom wall part 21a) of the internal space S1. Also, a width direction dimension of each of the vertical parts 221 is, as illustrated in FIG. 7, substantially the same as a width between facing surfaces of the front and back side wall parts 21d and 21e of the cell main body 21 (i.e., a Y axis direction dimension of the internal space S1). Note that a part indicated by thick lines in FIG. 7 is a part of the vertical part 221. On the basis of this, in the state where the vertical parts 221 of the applying electrodes 22 are inserted into the cell main body 21, substantially a whole of Y axis direction inner surfaces of the internal space S1 is configured to be covered by the applying electrodes 22.

Also, as illustrated in FIG. 3 and other drawings, upper end parts of the front and back side wall parts 21d and 21e of the cell main body 21 are configured to be lower than upper end parts of the left and right side wall parts 21b and 21c, and in the state where the applying electrodes 22 are inserted into the cell main body 21, upper surfaces of the horizontal parts 222 of the applying electrodes 22 are configured to be substantially flush with upper surfaces of the left and right side wall parts 21b and 21c.

The fixing spacer 23 is, as illustrated in FIGS. 2 to 5 and other drawings, a columnar one of which a cross section is substantially rectangular shaped, and as described above, inserted into the cell main body 21 from the longer direction one end part 21x; intervenes between the pair of applying electrodes 22 to thereby define the distance between the applying electrodes 22; and presses the pair of applying electrodes 22 against the inner surface of the cell main body 21 to thereby fix the applying electrodes 22 to the cell main body 21. Note that the fixing spacer is formed of fluororesin superior in corrosion resistance, such as PTFE.

Specifically, the fixing spacer 23 has, as illustrated in FIGS. 6 and 7, an insertion part 231 that is to be inserted into the cell main body 21, and an engaging part 232 that, in a state where the insertion part 231 is inserted into the cell main body 21, engages with the longer direction one end part 21x of the cell main body 21.

X axis direction side surfaces of the insertion part 231 are, as illustrated in FIG. 6, ones that come into contact with side surfaces of the applying electrodes 22 to define a distance between facing electrode surfaces 22A of the applying electrodes 22, and also presses the applying electrodes 22 against the left and right side wall inner surfaces of the cell main body 21 to fix the applying electrodes 22. That is, an X axis direction dimension of the insertion part 231 is one that is obtained by subtracting a thickness of the pair of applying electrodes 22 from an X axis direction dimension of the internal space S1. Also, a Y axis direction dimension of the insertion part 231 is, as illustrated in FIG. 7, substantially the same as the width between the facing surfaces of the front and back side wall parts 21d and 21e (i.e., the Y axis direction dimension of the internal space S1).

On the other hand, the engaging part 232 is provided in series with a longer direction one end part (Z axis direction upper end part) of the insertion part 231, and one that engages with the longer direction one end part 21x of the cell main body 21 to thereby define an insertion position of the insertion part 231 in the internal space S1 of the cell main body 21. The engaging part 232 has: front and back engaging parts 232a that come into contact with the upper end parts of the front and back side wall parts 21d and 21e; and left and right engaging parts 232b that come into contact with the upper end parts of the left and right side wall parts 21b and 21c. In particular, the left and right engaging parts 232b are positioned in upper parts of the applying electrodes 22 (see FIG. 6), and can therefore prevent the applying electrodes 22 from coming off from the cell main body 21.

Also, in the present embodiment, a longer direction length of the insertion part 231 is set to be shorter than the longer direction length of the internal space S1. As a result of this, in a state where the engaging part 232 engages with the longer direction one end part 21x, in a lower part of the internal space S1 of the cell main body 21, the zeta potential measuring space S2 in which the one pair of applying electrodes 22 are exposed is formed. The zeta potential measuring space S2 configured as described is a space having substantially a rectangular parallelepiped shape of which a lower surface corresponds to an inner surface of the bottom wall part 21a of the cell main body 21, an upper surface corresponds to a lower surface of the fixing spacer 23, left and right side surfaces correspond to the facing surfaces (electrode surfaces 22A) of the applying electrodes 22, and front and back side surfaces correspond to inner surfaces of the front and back side wall parts 21d and 21e. Also, in this case, the front and back side wall parts 21d and 21e that form the zeta potential measuring space S2 serve as the light introduction window 23 and the light lead-out window 24, respectively (see FIG. 7).

Also, the fixing spacer 23 is, as illustrated in FIG. 6 and other drawings, formed with: a sample introduction path 23a for externally introducing the liquid sample into the zeta potential measuring space S2; and a sample lead-out path 23b. The sample introduction path 23a and the sample lead-out path 23b are ones that are formed in parallel with each other along the longer direction and substantially linear-shaped. One end part of the sample introduction path 23a and one end part of the sample lead-out path 23b are both opened on an upper surface that forms the zeta potential measuring space S2, and their other end parts are opened on an upper surface of the fixing spacer 23. By forming the sample introduction path 23a and the sample lead-out path 23b in this manner, the liquid sample inside is prevented from leaking outside when the measuring cell 2 is used in an upright state (attached to the instrument main body).

Further, in a side wall of the fixing spacer 23, as illustrated in FIG. 7, a communicatively connecting hole 23h that makes a communicative connection between the sample introduction path 23a and an outer circumferential surface is formed, and also the communicatively connecting hole 23h that makes a communicative connection between the sample lead-out path 23b and the outer circumferential surface is formed. This enables insides of the sample introduction path 23a and the sample lead-out path 23b to be visually recognized from outside to check whether or not a bubble accumulates in the flow path 23a or 23b.

Note that in the case of flow measurement, the sample introduction path 23a and the sample lead-out path 23b should be provided; however, in the case of batch measurement, in particular, if the measuring cell 2 is disposable, and the contained liquid sample is not required to be discharged, it is not necessary to provide the sample lead-out path 23b. However, even in this case, if the sample lead-out path 23b is formed, it functions as an air vent port, and also the liquid sample can be introduced into the zeta potential measuring space S2 with use of the two flow paths, so that workability of sample introduction is improved.

Figure 8:
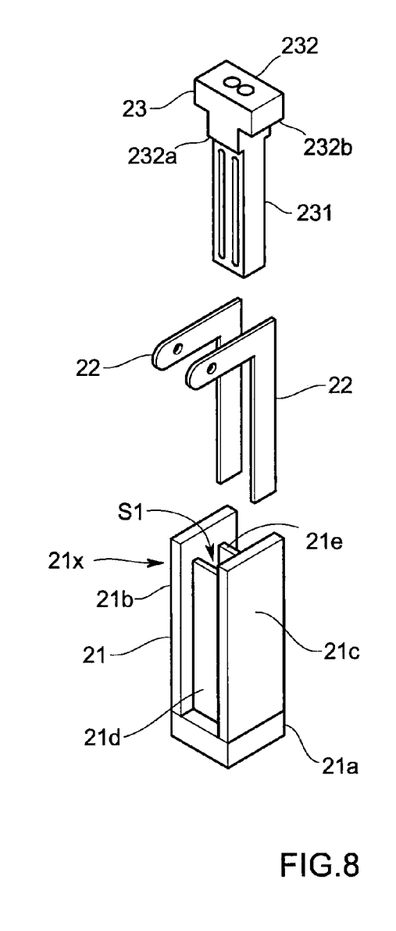
FIG. 8 is an exploded perspective view of the zeta potential measuring cell according to the same embodiment.

Next, a method for manufacturing the measuring cell 2 configured as described is briefly described referring to FIG. 8. First, the cell main body 21 is manufactured by glass welding of the bottom wall part 21a, the left and right side wall parts 21b and 21c, and the front and back side wall path 21d and 21e all made of quartz glass. Then, the applying electrodes 22 and the fixing spacer 23 that are preliminarily formed are inserted into the cell main body 21 from the longer direction one end part 23x, and thereby the applying electrodes 22 are fixed so as to be in close contact with inner surfaces of the left and right side wall parts 21b and 21c of the cell main body 21. At this time, the fixing spacer 23 is Inserted until the engaging part 232 thereof (front and back engaging parts 232a and left and right engaging parts 232b) comes into contact with the longer direction one end part 23x of the cell main body 21. As a result of this, the measuring cell 22 is manufactured. In addition, in the case of cleaning or replacing the applying electrodes 22, by removing the fixing spacer 23, only the applying electrodes 22 can be detached, and cleaned or replaced by different applying electrodes 22.

Effects of the Present Embodiment

According to the zeta potential measuring instrument 100 configured as described according to the present embodiment, the applying electrodes 22 and the fixing spacer 23 can be individually detached from the cell main body 21, and therefore cleaning work for the applying electrodes 22 can be simplified.

Also, in the case where it is necessary to replace the applying electrodes 22, such as the case where dirt of the applying electrodes 22 cannot be removed, the applying electrodes 22 can be replaced as a single body, and therefore the applying electrodes 22 can be replaced at low cost. In this case, only by inserting the pair of applying electrodes 22 and the fixing spacer 23 into the cell main body 21, the zeta potential measuring space S2 is formed in the cell main body 21, and therefore assembling of the zeta potential measuring cell 2 is easy.

Further, the applying electrodes 22 that undergo different surface treatment or are made of a different material corresponding to the type of the liquid sample can be manufactured as a single body; the replacement thereof is easy; and the zeta potential measuring cell 2 specialized for the type of any of various liquid samples can be easily manufactured.

In addition, it is not necessary to manufacture a unit that is supposed to have the pair of applying electrodes 22, and also it is only necessary to manufacture the applying electrodes 22 as a single body and the fixing spacer 23 as a single body, so that manufacturing cost can also be reduced.

Other Variations

Note that the present invention is not limited to the above-described embodiment.

For example, the internal space in the above-described embodiment is substantially quadrangular prism shaped; however, besides, it may be substantially polygonal prism shaped, or substantially columnar shaped.

Also, each of the applying electrodes in the above-described embodiment is substantially L-shaped in a side view; however, besides, it may be rectangular shaped in a side view.

Further, in the above-described embodiment, the engaging part is one that has the left and right engaging parts and the front and back engaging parts; however, it may be only required to have any one of the two sets of engaging parts.

In addition, in the above-described embodiment, the zeta potential measuring instrument is described; however, the present invention can also be applied to an instrument that makes a measurement of a particle physical property other than the zeta potential.

Besides, it should be appreciated that the present invention is not limited to any of the above-described embodiments, but can be variously modified without departing from the scope thereof.

The invention claimed is:

1. A particle characterization cell used for a particle characterization instrument that measures physical properties of particles dispersed in a liquid sample, the particle characterization cell being configured to comprise:
   a bottom-equipped tubular cell main body that forms an internal space that extends in a longer direction, and has a longer direction one end part that is opened;
   a pair of applying electrodes that are inserted into the cell main body from the longer direction one end part and arranged so as to face to each other in the internal space; and
   a fixing spacer that is inserted into the cell main body from the longer direction one end part, intervenes between the pair of applying electrodes to thereby define a distance between the applying electrodes, and presses the pair of applying electrodes against an inner surface of the cell main body to thereby fix the pair of applying electrodes, wherein in a state where the fixing spacer is inserted into the cell main body, in a lower part of the internal space of the cell main body, a particle characterization space in which the pair of applying electrodes is exposed is formed, wherein the cell main body is formed with a light introduction window that introduces the laser light into the particle characterization space.

2. The particle characterization cell according to claim 1, wherein:

the fixing spacer has an insertion part that is to be inserted into the cell main body, and an engaging part that, in a state where the insertion part is inserted into the cell main body, engages with the longer direction one end part; and the insertion part is shorter than a longer direction length of the internal space.

3. The particle characterization cell according to claim 1, wherein the fixing spacer has a sample introduction path that externally introduces the liquid sample into the particle characterization space.

4. A particle characterization instrument comprising the particle characterization cell according to claim 1.

5. The particle characterization cell according to claim 1, wherein:

the cell main body is formed with a light lead-out window for leading the scattered light having passed through the particle characterization space, wherein, the light introduction window and the light lead-out window are formed in a position of the cell main body different from a position of the pair of applying electrodes.

\* \* \* \* \*